United States Patent
Kokubo et al.

(10) Patent No.: US 6,429,024 B1
(45) Date of Patent: Aug. 6, 2002

(54) TEST METHOD FOR IGA NEPHROPATHY

(75) Inventors: Tohru Kokubo, Kanagawa; Kenji Arai, Shizuoka; Kazunori Toma, Kanagawa, all of (JP)

(73) Assignee: Asahi Kasei Kabushiki Kaisha, Osaka (JP)

(*) Notice: Subject to any disclaimer, the term of this patent is extended or adjusted under 35 U.S.C. 154(b) by 0 days.

(21) Appl. No.: 09/646,154

(22) PCT Filed: Mar. 25, 1999

(86) PCT No.: PCT/JP99/01525

§ 371 (c)(1),
(2), (4) Date: Nov. 13, 2000

(87) PCT Pub. No.: WO99/50663

PCT Pub. Date: Oct. 7, 1999

(30) Foreign Application Priority Data

Mar. 31, 1998 (JP) .............................. 10-101759

(51) Int. Cl.[7] .................. G01N 33/543; G01N 33/545; G01N 33/546; G01N 33/564

(52) U.S. Cl. ................. 436/506; 435/7.1; 435/7.24; 435/7.92; 435/7.93; 436/507; 436/513; 436/528; 436/531; 436/534; 436/811; 530/326; 530/330

(58) Field of Search ................ 435/7.1, 7.24, 435/7.92, 7.93, 7.94, 7.95; 436/506, 513, 518, 528, 531, 534, 536, 172, 811, 507; 530/326, 330

(56) References Cited

FOREIGN PATENT DOCUMENTS

| JP | 9-311132 | 12/1997 |
|---|---|---|
| WO | WO 88/08983 | 11/1988 |

OTHER PUBLICATIONS

Hitoo Iwase, Atsushi Tanaka, Yoshiyuki Hiki, Tohru Kokubo, Ikuko Ishii–Karakasa, Yutaka Kobayashi and Kyoko Hotta, "Estimation of the Number of O–Linked Oligosaccharides Per Heavy Chain of Human Serum IgA1 by Matrix–Assisted Laser Desorption Ionization Time–of–Flight Mass Spectrometry (MALDI–TOFMS) Analysis of the Hinge Glycopeptide", J. Biochem, vol. 120, No. 1, 1996, pp. 393–397.

Akira Horii, Yoshiyuki Hiki, Michiyo Saitoh, Akira Kanamori, Hitoo Iwase, Kyoko Hotta and Yutaka Kobayashi, "Binding of IgA1 to Monocyte/Macrophage Cell Lines (THP–1,U937) in IgA Nephropathy –A Possible Role of O–Glycan in the IgA1 Molecule–", vol. 37, 1995, pp. 558–563, Translated Abst. only.

J. Berger et al., "Les dépôts intercapillaires d'IgA–IgG," J. Urol., vol. 74, pp. 694–695, 1968.

M.E. Conley et al., "Selective Deposition of Immunoglobulin $A_1$ in Immunoglobulin A Mephropathy, Anaphylactoid Purpura Nephritis, and Systemic Lupus Erythematosus," J. Clin. Invest., vol. 66, Dec. 1980, pp. 1432–1436.

B. Frangione et al., "Partial Duplication in the "Hinge" Region of $IgA_1$ Myeloma Proteins," Proc. Nat. Acad. Sci. USA, vol. 69, No. 12, pp. 3673–3676, Dec. 1972.

Basic immunology, Upper vol., pp. 158–162, 1986, The University Tokyo Press, Trans. Section Only.

J. Baenziger et al., "Structure of the Carbohydrate Units of $IgA_1$ Immunoglobulin," The Journal of Biological Chemistry, vol. 249, No. 22, Nov. 25, 1974, pp. 7270–7281.

J. Am. Renal. Soc. 8, p. 538A, 1997, Abstract #A2506, Kokube et al.

Y. Kotera et al., "Humoral Immunity against a Tandem Repeat Epitope of Human Mucin MUC–1 in Sera from Breast, Pancreatic and Colon Cancer Patients," Cancer Research, vol. 54, pp. 2856–2860, Jun. 1, 1994.

Enzyme immunoassay (EIA) Proteins, Nucleic Acids and Enzymes, Supplement No. 31, Enzyme immunoassay, pp. 13–26, 1987, Translated Section Only.

Latex aggulutination photometric immunoassay; LAPIA, I. Sakurabayashi et al., Nihon Rinsho, vol. 48, Supplement, pp. 1356–1361, 1990, Transl. Sect. Only.

Nephelometric immunoassay; NIA, Y. Yamagishi et al., Rinsho–Kensa (Clinical Examinations), vol. 23, Supplement, pp. 1286–1289, 1979, Trans. Sect. Only.

Latex slide agglutination, S. Shibata et al., Equipment and Reagents, vol. 11, pp. 338–342, 1988, Trans. Sect. Only.

Counting immunoassay; CIA, K. Hashimoto et al., Test and Technology, vol. 22, No. 5, pp. 67–68, 1994, Transl. Sect. Only.

Turbidimetric immunoassay: TIA, T. Toyama, Clinical pathology, vol. 35, pp. 868–873, 1987, Trans. Sect. Only.

Luminescent immunoassay; LIA, Proteins, Nucleic Acids and Enzymes, Supplement 31, Enzyme immunoassay, pp. 252–263, 1987, Transl. Sect. Only.

Fluorescence polarization immunoassay; FPIA, K. Kurata, New case studies on immunoassay and application for development of diagnostic reagents and therapeutic agents, Keiei–Kyoiku Publ., Jun. 20, 1985, pp. 91–102, Trans. Sect. Only.

(List continued on next page.)

Primary Examiner—Christopher L. Chin
Assistant Examiner—James L. Grun
(74) Attorney, Agent, or Firm—Young & Thompson

(57) ABSTRACT

A test method for IgA nephropathy involves determining antibody, which recognizes the core peptide of the hinge region in IgA1, in specimens. The method is a rapid and sample test method for IgA nephropathy having less emotional distress for the patients, low risk for peripheral hemorrhage of the kidney and reduced financial burden for the patients.

3 Claims, 4 Drawing Sheets

OTHER PUBLICATIONS

Immunoelectrophoresis, I. Urushizaki, New case studies on immunoassay and application for development of diagnostic reagents and therapeutic agents, Keiei–kyoiku, Publ., Jun. 20, 1985, pp. 63–72, Trans. Sect. Only.

Spin immunoassay; SIA, H. Sayo, New case studies on immunoassay and application for development of diagnostic reagents and therapeutic agents, Keiei–Kyoiku, Publ., Jun. 20, 1985, pp. 52–62, Trans. Sect. Only.

Fluorescence immunoassay; FIA, T. Hashimoto et al., Test and Technology, vol. 22, No. 5, pp. 61–66, 1994, Transl. Sect. Only.

Radioimmuoassay; RIA, K. Kurata, New case studies on immunoassay and application for development diagnostic reagents and therapeutic agents, Keiei–Kyoiku, Publ., Jun. 20, 1985, pp. 33–41, Trans. Sect. Only.

TEST METHOD FOR IGA NEPHROPATHY

This application is a 35 U.S.C. 371 filing of PCT/JP99/01525 filed Mar. 25, 1999.

BACKGROUND OF THE INVENTION

1. Field of the Invention

This invention relates to a novel test method for IgA nephropathy. More particularly, the present invention pertains to a rapid and simple test method for IgA nephropathy and a determination method of antibody, which has low risks in emotional distress, peripheral hemorrhage in the kidney and financial burden to the patient, by determining antibody recognizing IgA1 hinge region core peptide in the specimen.

2. Description of Related Art

IgA (immunoglobulin A) nephropathy is a disease concept provided by Berger et al. (J. Urol., 74, pp. 694–695, 1968), and is a primary glomerular nephritis having features with clinically poor symptoms except for continuous proteinuria and hematuria, and histological features with precipitants consisting of mainly IgA in the mesangium. The incidence of IgA nephropathy in Japan is high and accounts for 30% of the chronic nephritis. The long term prognosis is not so favorable, and 10–15% of patients with 10 years progress and about 30% of patients with 20 years progress suffer from terminal renal failure. Consequently, IgA nephropathy is especially noticed as a causal disease for terminal renal failure.

At present, the only known test method for IgA nephropathy is the renal biopsy. This test method, however, causes emotional distress for the patients, and further may cause peripheral hemorrhage in the kidney after the biopsy. In addition, the patients must have absolute rest for more than 24 hours after the renal biopsy, and this requires the patients to stay in hospital for several days, and this causes a heavy financial burden for them. Furthermore, the test method has disadvantages including requiring many kinds of test facilities together with long term testing time.

Consequently, a test method for IgA nephropathy is desired, which is simple and operable within a short time as well as giving less emotional distress, without risk of peripheral hemorrhage of kidney and with less financial burden.

PROBLEMS TO BE SOLVED BY THE INVENTION

An object of the present invention is to provide a rapid and simple test method for IgA nephropathy. Such a test method requires no renal biopsy, which has been essential in the conventional test method for IgA nephropathy. The test method is comprised of detecting antibody, which recognizes the core peptide of the hinge region in IgA1, in specimens. As a result, the patients' emotional distress, risk of peripheral hemorrhage of the kidney and the financial burden can be reduced.

MEANS FOR SOLVING THE PROBLEMS

We have made various trials for solving the above problems and have found a rapid and simple test method for IgA nephropathy and a determination method for antibody, which recognizes the core peptide of hinge region in IgA1, and completed the present invention. Such a test method is comprised of detecting antibody, which recognizes the core peptide of the hinge region in IgA1, in specimens. As a result, the patients' emotional distress, risk of peripheral hemorrhage of the kidney and the financial burden can be reduced.

The present invention relates to a test method for IgA nephropathy by detecting antibody recognizing the core peptide of the hinge region in IgA1 in specimens. According to preferred embodiments of the present invention, a test method comprising detecting antibody recognizing the core peptide of the hinge acid sequence consisting of region having at least a part of amino acid sequence consisting of Pro Val Pro Ser Thr Pro Pro Thr Pro Ser Pro Ser Thr Pro Pro Thr Pro Ser Pro Ser Cys (SEQ ID NO: 1)

or at least three amino acids thereof. According to a further preferred embodiment of the present invention, the test method comprises using an immobilized solid phase core peptide of the hinge region, said immobilized solid phase of which is microtiter plate or latex particles.

Examples of detection methods for the antibody of the present invention are test method for IgA nephropathy which includes enzyme immunoassay, latex agglutination photometric immunoassay, nephelometric immunoassay, latex slide agglutination test, turbidimetric immunoassay, luminescent immunoassay, fluorescence polarization immunoassay, fluorescence immunoassay and radioimmunoassay.

The present invention is explained in detail with reference to the drawings as follows.

FIG. 1 illustrates a schematic drawing showing the outline of a molecular structure of IgA1.

IgA, which may be involved in a cause for IgA nephropathy, is a type of immunoglobulin. The IgA molecule consists of two heavy chains and two light chains, and is classified into subtypes of IgA1 and IgA2 depending on the difference in heavy chain structures.

In IgA nephropathy, since the deposited IgA in the glomeruli is mainly IgA1 subtype (Conley et al., J. Clin. Invest. 66, pp. 1432–1436, 1980), the properties of IgA1 between those of patients with IgA nephropathy and those of healthy subjects or patients with non-IgA nephropathy may differ from one another.

The largest structural difference between IgA1 and IgA2 exists in the hinge region of the heavy chain. The hinge region of IgA2 is deficient in 13 amino acids (Frangione et al., Proc. Natl. Acad. Sci. USA, 69, pp. 3673–3676, 1972) as compared with the hinge region of IgA1 (SEQ ID NO: 13) [Basic immunology, Upper Vol., pp. 158–162, (1986), The University Tokyo Press].

Baenziger et al. reported that an O-linked sugar chain is bonded to five serine residues of the hinge region in IgA1 molecule (J. Biol. Chem. 249, pp. 7270–7281, 1974).

We have demonstrated that the binding ability between the antibody obtained from rabbit immunized with synthetic peptide of the hinge region in IgA1 and the serum IgA1 of patients with IgA nephropathy was higher than the binding ability between the above antibody and the serum IgA1 of healthy subjects or patients with non-IgA nephropathy. As a result, we have reported that IgA1 of the patients with IgA nephropathy was abnormal in the O-linked sugar chain bound to the hinge region, and in conclusion, the core peptide of the hinge region (core peptide of hinge region means the peptide constructing the hinge region) was in an exposed state (J. Am. Renal. Soc. 8, pp. 538 A, 1997).

The core peptide of the hinge region has structural similarity with mucin insofar as containing large amounts of proline, serine and threonine.

The immunologically activating ability of human mucin core peptide has been known. For example, Kotera et al.

reported that the mucin which is frequently expressed in some types of cancer cells has less sugar chain, and, as a result, immune reaction against the exposed core peptide occurs in the host (Cancer Res., 54, pp. 2856–2860, 1994).

We have made extensive studies based on the above findings. As a result, we have found that, in patients with IgA nephropathy, O-linked sugar chain bonded with the hinge region of IgA1 is decreased, and this results in exposing the core peptide of the hinge region, such that an immune reaction against the core peptide of the hinge region in IgA1 is generated and the antibody titer recognizing the core peptide of the hinge region in IgA1 is increased; and that these findings can be applied for testing IgA nephropathy, and completed the present invention.

A rapid test for IgA nephropathy can be performed by determining antibody, which recognizes the core peptide of the hinge region of IgA1, in specimens such as body fluid of the patients. Namely, the present invention relates to a test method for IgA nephropathy based on determining antibody, which recognizes the core peptide of the hinge region in IgA1, in specimens.

In the present invention, the hinge region of IgA1 indicates the region between CH1 domain and CH2 domain in the heavy chains, which construct IgA1 molecule, and may optionally include a structure having added thereto a sequence of Pro-Val—in the N-terminal region.

This region contains disulfide bond between heavy chains, and is rich in proline, serine and threonine.

In the present invention, the core peptide of the hinge region in IgA1 as an antigen can include the peptide constructing the hinge region in IgA1 or a partial structure thereof.

Amino acid sequences of the peptide of the formula (SEQ ID NO: 1),

```
Pro Val Pro Ser Thr Pro Pro Thr Pro

Ser Pro Ser Thr Pro Pro Thr Pro Ser

Pro Ser Cys
``` or peptides having partial structure thereof consisting of at least three amino acids thereof are preferably used. Examples of peptides are peptides comprising amino acid sequences of the formulas:

```
Val Pro Ser, Ser Thr Pro, Thr Pro Pro,

Pro Pro Thr, Pro Thr Pro, Thr Pro Ser,

Pro Ser Pro, Ser Pro Ser or Pro Ser Thr.
```

More preferably, peptides consisting of at least five amino acids, for example, formulas,
  ProValProSerThr (SEQ ID NO: 2),
  ProSerThrProPro (SEQ ID NO: 3),
  ThrProProThrPro (SEQ ID NO: 4),
  ProThrProSerPro (SEQ ID NO: 5),
  ProSerProSerThr (SEQ ID NO: 6), or
  ProSerProSerCys (SEQ ID NO: 7)
can be mentioned.

In the present invention, so far as enabling, all peptides or proteins including peptide constructing the hinge region of IgA1 or a part thereof can be used.

Further, the core peptide of the hinge region in IgA1 modified by sugars, lipids, functional groups, protective groups or cross linking agents, and bound to carrier such as proteins, plastics or latex particles can be used.

In the present invention, any core peptide of the hinge region in IgA1, i.e. antigen, produced by any method, for example, a product by synthesis, a product derived from IgA1 originated from patients or subjects with non-IgA nephropathy, or a product by gene recombinant technology, can be used.

Examples of specimens in the present invention are biological fluid such as blood, plasma, serum, saliva or urine, biological tissue extracts and supernatant solutions of the tissue culture.

Specimens can be used without dilution or with aliquot dilution of buffer solution depending on the principle of detection method, detection sensitivity, detection range and other factors in the present invention.

Specimens can contain anticoagulants such as sodium EDTA, sodium citrate or heparin sodium, materials for stabilizing the specimen, or other substances.

With respect to buffer solutions used in the present invention, buffers which are customarily used in immunological determination methods and preferably have a pH value in the range of from 5 to 9 can be employed.

For example, phosphate buffer, borate buffer, carbonate buffer, Tris-HCl buffer, veronal buffer and Good's buffer such as HEPES buffer, PIPES buffer and MES buffer, can be used.

For the purpose of preventing non-specific adsorption of proteins to the carrier used in the determination method of the present invention such as microtiter plate and latex, any type of additives, for example, bovine serum albumin (BSA), protein such as gelatin or skimmed milk, surface active agents, sugars, chelating agents, reducing agents or salt can be added in the buffer solution.

The concentration of the additives can be selected from the concentration used in the immunological determination method of antibody, which is applied in known antigen-antibody reactions.

Examples of antibody to be determined in the present invention are all antibodies that react with the core peptide of the hinge region in IgA1 in specimens, and are preferably IgG class, IgM class or IgA class.

In the present invention, a method for immunologically determining the antibody, which recognizes the core peptide of the hinge region in IgA1 as the antigen, in specimens, is characterized by reacting the above described core peptide of the hinge region in IgA1 with the specimen under the condition to form antigen-antibody complex and qualitating or quantitating the antibody, which recognizes the core peptide of the hinge region in IgA1, in the specimen based on assaying the thus generated product of the antigen-antibody reaction.

For example, enzyme immunoassay (EIA) (Proteins, Nucleic Acids and Enzymes, Supplement No. 31, Enzyme immunoassay, pp. 13–26, 1987) can be used.

In one embodiment, a carrier having immobilized thereon core peptide of the hinge region in IgA1 and a specimen are reacted, and a labeled antibody (a complex of anti-human IgG antibody, anti-human IgM antibody, anti-human IgA antibody or fragments thereof having binding activity to antigen and labeled enzyme) is reacted therewith, then the coloring agent (substrate) for developing color by applying the reaction with labeled enzyme bound with the carrier through the antigen-antibody complex, is added and subjected to reaction.

The reaction is terminated, if necessary, by adding enzyme reaction terminator, and optical absorption of the thus generated coloration is measured at a suitable wavelength to quantitatively or qualitatively assay the antibody, which recognizes the core peptide of the hinge region in IgA1, in the specimen.

In a further detailed embodiment, in case that a complex bound with the synthetic core peptide of the hinge region in IgA1 consisting of peptide of at least three amino acids, preferably at least five amino acids, selected from the amino acid sequence of the core peptide of the hinge region in IgA1 such as amino acid sequence of the formula,

```
Pro Val Pro Ser Thr Pro Pro Thr Pro

Ser Pro Ser Thr Pro Pro Thr Pro Ser

Pro Ser Cys (SEQ ID NO: 1)
``` and the bovine serum albumin (BSA) at a binding ratio of 1:1–15:1 (peptide:BSA), preferably, 1:1–10:1 (peptide:BSA), is used as an antigen, the antigen adjusted within a concentration range generally from 0.01 μg/ml–100 μg/ml is added to the plastic microtiter plate, generally at 25 μl–200 μl/well, allowed to stand at 4° C.–40° C., for 10 min.–48 hours washed with suitable buffer to immobilize the antigen. Further, the specimens (such as serum of the patients) diluted with suitable buffer, generally 25 μl–200 μl, are added to the microtiter plate with the immobilized antigen, and allowed to stand generally at 4° C.–40° C., for 5 min.–48 hours then are washed with suitable buffer.

Next, the self-known labeled antibody (a complex of anti-human IgG antibody, anti-human IgM antibody, anti-human IgA antibody or fragments thereof having binding activity to antigen, and the labeling enzyme, for example generally used in the enzyme immunoassay, such as peroxidase, alkaline phosphatase, β-galactosidase or glucose oxidase) diluted with suitable buffer, generally 25 μl–200 μl, is added and allowed to react generally at 4° C.–40° C., 10 min.–48 hours then are washed with suitable buffer.

Further, coloring agent (substrate) for developing color with a reaction of the labeled enzyme is added generally 25 μl–200 μl, and is reacted generally within a range at 4° C.–40° C., for 1 min.–48 hours.

The reaction is terminated, if necessary, by adding enzyme reaction terminator. Optical absorbancy of the supernatant of the enzymatic reaction mixture is colorimetrically measured and the antibody recognizing the core peptide of the hinge region in IgA1 in the specimen is qualitatively or quantitatively measured.

In the above, in case that peroxidase is selected as the labeled enzyme, orthophenylenediamine and the like can be used as a substrate, and the resultant coloring of the enzyme reaction is measured by absorbancy at 490 nm.

Further, in case that alkaline phosphatase is selected as the labeled enzyme, paranitrophenyl phosphate can be used as a substrate, and the resultant color development of the enzyme reaction is measured by absorbancy at 405 nm.

If the antibody titer, which recognizes the core peptide of the hinge region in IgA1 (IgG class antibody titer, IgM class antibody titer or IgA class antibody titer), is high, the above absorbancy values are also high.

For example, the examination for IgA nephropathy can be performed as follows: the absorbancy of the specimens obtained from the healthy subjects or patients with non-IgA nephropathy, or the concentration values in these specimens, which are quantitatively determined by comparing the obtained absorbancy with the calibration curve calculated from the standard substance, are obtained. Measurement above the average of these values+2×standard deviation are deemed to be positive, and those below or not above the value thereof are considered to be negative. Using these criteria, the examination of subjects, whether or not the patient is suffering from IgA nephropathy, can be determined by detecting the absorbancy of the patients or the quantitative value of concentration obtained from the same manner as above.

The determination method is not limited within the enzyme immunoassay, and all methods, which can determine antibody recognizing the core peptide of the hinge region in IgA1, can be used in the present test method. Examples thereof are as follows:

(a) Conventionally used latex agglutination photometric immunoassay; LAPIA (Sakurabayashi, 1. et al., Nihon Rinsho, Vol. 48, supplement, pp. 13 56–1361, 1990). Latex particles immobilized with the core peptide of the hinge region in IgA1 and a specimen are mixed. Turbidity generated from the result of antigen-antibody reaction is measured as absorbancy. The antibody recognizing the core peptide of the hinge region in IgA1 in the specimen is determined quantitatively or qualitatively based on measurement of changes of the absorbancies.

(b) Nephelometric immunoassay; NIA (Yamagishi, Y. et al., Rinsho-Kensa (Clinical Examinations), Vol. 23, Supplement, pp.1286–1289, 1979). Latex particles immobilized with the core peptide of the hinge region in IgA1 are mixed with a specimen. The thus produced antigen-antibody complex is irradiated with light (laser) and changes of the scattering strength are measured, and the antibody recognizing the core peptide of the hinge region in IgA1 in the specimen is quantitatively or qualitatively measured.

(c) Latex slide agglutination (Shibata, S. et al., Equipment and Reagents, Vol. 11, pp. 338–342, 1988). Latex particles immobilized with the core peptide of the hinge region in IgA1 and a specimen are mixed on the plate, and agglutination of latex particles generated as a result of antigen-antibody reaction is confirmed macroscopically to qualitate the antibody, which recognizes the core peptide of the hinge region in IgA1, in the specimen.

(d) Counting immunoassay; CIA(Hashimoto, K. et al., Test and Technology, Vol. 22, No. 5, pp. 67–68, 1994). Latex particles immobilized with the core peptide of the hinge region in IgA1 and a specimen are mixed. Sizes and numbers of aggregates generated as a result of antigen-antibody reaction are measured. The antibody recognizing the core peptide of the hinge region in IgA1 in the specimen can be qualitatively or quantitatively measured.

(e) Turbidimetric immunoassay; TIA (Toyama, T., Clinical pathology, Vol. 35, pp. 868–873, 1987). The core peptide of the hinge region in IgA1 and a specimen are mixed. Turbidity generated as a result of antigen-antibody reaction is measured and changes of absorbancy are measured to qualitate or quantitate the antibody recognizing the core peptide of the hinge region in IgA1 in the specimen.

(f) Luminescent immunoassay; LIA ("Proteins, Nucleic Acids and Enzymes", Suppl. 31, "Enzyme Immunoassay", pp. 252–263, 1987).

(g) Fluorescence polarization immunoassay; FPIA (Kurata, K., "New case studies on immunoassay and application for development of diagnostic reagents and therapeutic agents", Keiei-Kyoiku Publ., Jun. 20, 1985, pp. 91–102).

(h) Immunoelectrophoresis (Urushizaki, I. et al., "New case studies on immunoassay and application for development of diagnostic reagents and therapeutic agents", Keiei-Kyoiku Publ., Jun. 20, 1985, pp. 63–72).

(i) Spin immunoassay; SIA (Sago, H., "New case studies on immunoassay and application for development of diagnostic reagents and therapeutic agents", Keiei-Kyoiku Publ., Jun. 20, 1985, pp. 52–62).

(j) Fluorescence immunoassay; FIA (Hashimoto, T. et al., Test and Technology, Vol. 22, No. 5, pp. 61–66, 1994), and (k) Radioimmunoassay; RIA (Kurata,K., "New case studies on immunoassay and application for development of diagnostic reagents and therapeutic agents", Keiei-Kyoiku Publ., Jun. 20, 1985, pp. 33–41).

Qualitative and quantitative assay methods for a product of antigen-antibody reaction in the present invention are not limited to those performed by manual operation but can be performed by applying automatic analysis.

In the enzyme immunoassay, in case of determining antibody recognizing the core peptide of the hinge region in IgA1 in specimens using microtiter plate immobilized with the core peptide of the hinge region in IgA1, for example, BECKMAN Biomek 1000 Automated Laboratory Workstation (Beckman Inc.) or CELL ASSAY-2000 ROBOTIC ASSAY SYSTEM (Moritex Inc.), both of which are automated system equipment with supplying specimens, supplying reagents, washing operation, measurement of absorbancy and data processing, can be used.

In detail, a specimen, enzyme labeled antibody and substrate solution are added, in this order, together with washing operation among each addition, in the microtiter plate immobilized with the core peptide of the hinge region in IgA1, and the reaction is terminated, if necessary, by adding a terminator for enzyme reaction, then absorbancy of the color development as a result of the enzyme reaction between the labeled enzyme and substrate used is measured at appropriate wave length selected from the customary measurement conditions to determine the antibody recognizing the core peptide of the hinge region in IgA1 in the specimen.

In the latex agglutination photometric immunoassay, in order to determine antibody, which recognizes the core peptide of the hinge region in IgA1 in specimen by using latex particles having immobilized thereon the core peptide of the hinge region in IgA1, for example, a Hitachi 705, 7050, 7150, 736 or 7070 automatic analyzer, which are automatic equipment systems for supplying specimens, supplying reagents, measurement of absorbance and data processing, can be used.

In detail, latex particles immobilized with the core peptide of the hinge region in IgA1 and a specimen are mixed in a reaction cell, and the blank is corrected by measuring with suitable wave length selected from the known measurement conditions, preferably at 400 nm–950 nm, then changes of absorbancy after a constant time are measured to determine antibody recognizing the core peptide of the hinge region in IgA1 in the specimen.

In the method of the present invention, measurement operations may be facilitated if the necessary reagents for practicing the present invention are prepared in a kit. Further, it is convenient to practice the present invention using automated analytical equipment.

Example of reagent kits used in the present invention is a kit comprising a combination of a carrier (such as microtiter plate or latex particles) immobilized with the core peptide of the hinge region in IgA1 and reagents necessary for practice in the present invention such as buffer, standard substance, labeled antibody, substrate, solubilizing agent for substrate or reaction terminator.

MODE FOR CARRYING OUT THE INVENTION

Figure 1:
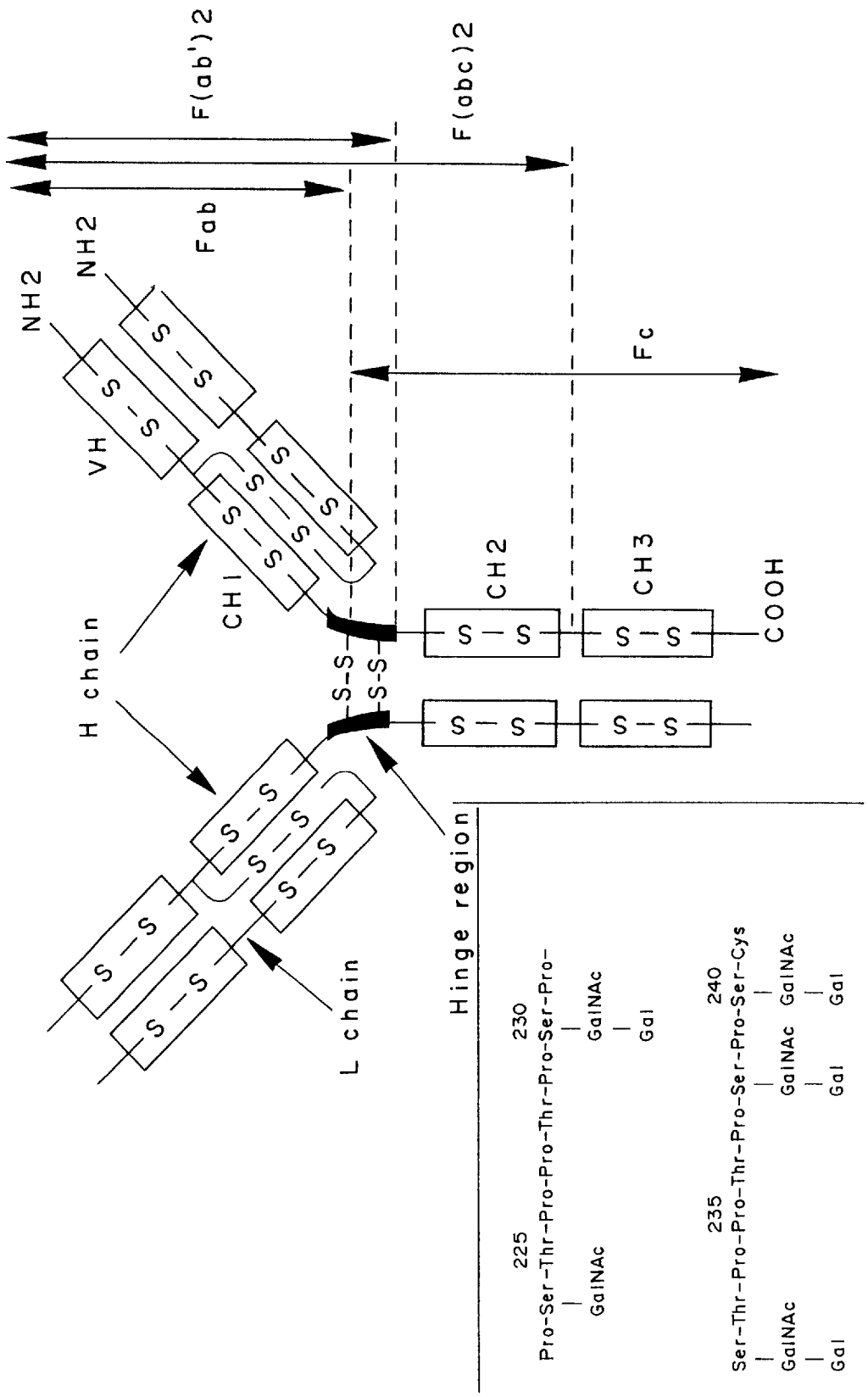
FIG. 1 is a schematic drawing showing the outline of a molecular structure of IgA1.

Examples of the present invention are illustrated in detail with reference to the drawings, but the present invention is not restricted by these examples.

EXAMPLE 1

(1) Preparation of Antigen

BSA (bovine serum albumin, purchased from SIGMA Inc.) was dissolved to 13.4 mg/ml with PBS (0.01 M phosphate buffer, pH 7.2, containing 0.15 M NaCl), and 1.5 ml thereof was added to 15 ml plastic centrifugal tube (purchased from Sumitomo Bakelite Co.). A solution (1001 μl) of EMCS (N-(ε-maleimidocaproyloxy) succinimide, purchased from Dojin Chemical Lab. Inc.) in DMSO (dimethyl sulfoxide purchased from Wako Pure Chemicals Co.) (100 mg/ml) was added to the above BSA solution, and incubated at room temperature for 60 minutes.

The incubation mixture was charged on an Econo-Pac IODG column (purchased from Bio-Rad Inc.) equilibrated with PBS, and eluated with PBS. Each 1 ml of the eluates was fractionated into 15 ml plastic centrifugal tube (purchased from Sumitomo Bakelite Co.), and absorbancy was measured at 280 nm to collect the protein fractions.

A solution (250 μl) of synthetic core peptide of the hinge region in IgA1

```
Pro Val Pro Ser Thr Pro Pro Thr Pro

Ser Pro Ser Thr Pro Pro Thr Pro Ser

Pro Ser Cys (SEQ ID NO: 1)
```

(molecular weight 2031.3) (synthesized in Acord Inc.) in PBS (20 mg/ml) was added to the above collected protein fraction (3 ml) and incubated at 4° C. for 36 hours.

The incubation mixture was charged on the Econo-Pac IODG column equilibrated with PBS and eluated with PBS. Each 1 ml of the eluates was fractionated in the 15 ml plastic centrifugal tube(purchased from Sumitomo Bakelite Co.), and was measured absorbancy at 280 nm and the protein fractions were collected to obtain a protein solution (19.3 mg/ml, 3 ml). The obtained solution was used as an antigen in the following experiments.

(2) Measurement of Antibody Titer

The above antigen solution was dissolved to 10 μg/ml in 0.015 M carbonate buffer (pH 9.6) and each 100 μl was added in each well of the 96 well microtiter plate (A Flow General Co., Linbro/Titertek EIA Microtitration plate, Cat. No. 76-381-04), then incubated at 4° C. overnight (standing culture).

PBS (0.01 M phosphate buffer, pH 7.5, containing 0.15 M NaCl) solution (200 μl) containing 1% bovine serum albumin (fraction V, purchased from SIGMA Inc.) was added in each well, and incubated at 4° C. overnight. Each well was washed with 200 μl of PBS. Sera of 32 cases in a group of patients with IgA nephropathy and sera of 32 cases in a group of patients with non-IgA nephropathy (a group of patients with kidney diseases without IgA nephropathy) were diluted to 1/100 with PBS, and the diluted solution (each 100 μl) was added in each well. After incubation at room temperature for 3 hours, each well was washed three times with PBS (200 μl) containing 0.1% bovine serum albumin and 0.05% Tween-20.

A solution (100 μl) of peroxidase labeled anti-human IgG (purchased from Organon Tecknika Inc.) or a solution (100 μl) of peroxidase labeled anti-human IgM (purchased from Organon Tecknika Inc.), each of which was diluted to 1/200 with PBS, was added in each well.

After incubation at room temperature for 1 hour, each well was washed three times with PBS (200 μl) containing 0.1% bovine serum albumin and 0.05% Tween-20.

Coloring agent (100 μl)(orthophenylenediamine 20 mg, sodium dihydrogen phosphate $12H_2O$ 1.795 g, citric acid 0.525 g, and hydrogen peroxide 15 μl were dissolved in water 50 ml) was added in each well, and incubated at room temperature for 1 hour.

Absorbancy at 490 nm was measured using a microplate reader (Bio-Rad Inc., Microplate reader Model 450).

(3) Result of IgG Class Antibody Titer

Figure 2:
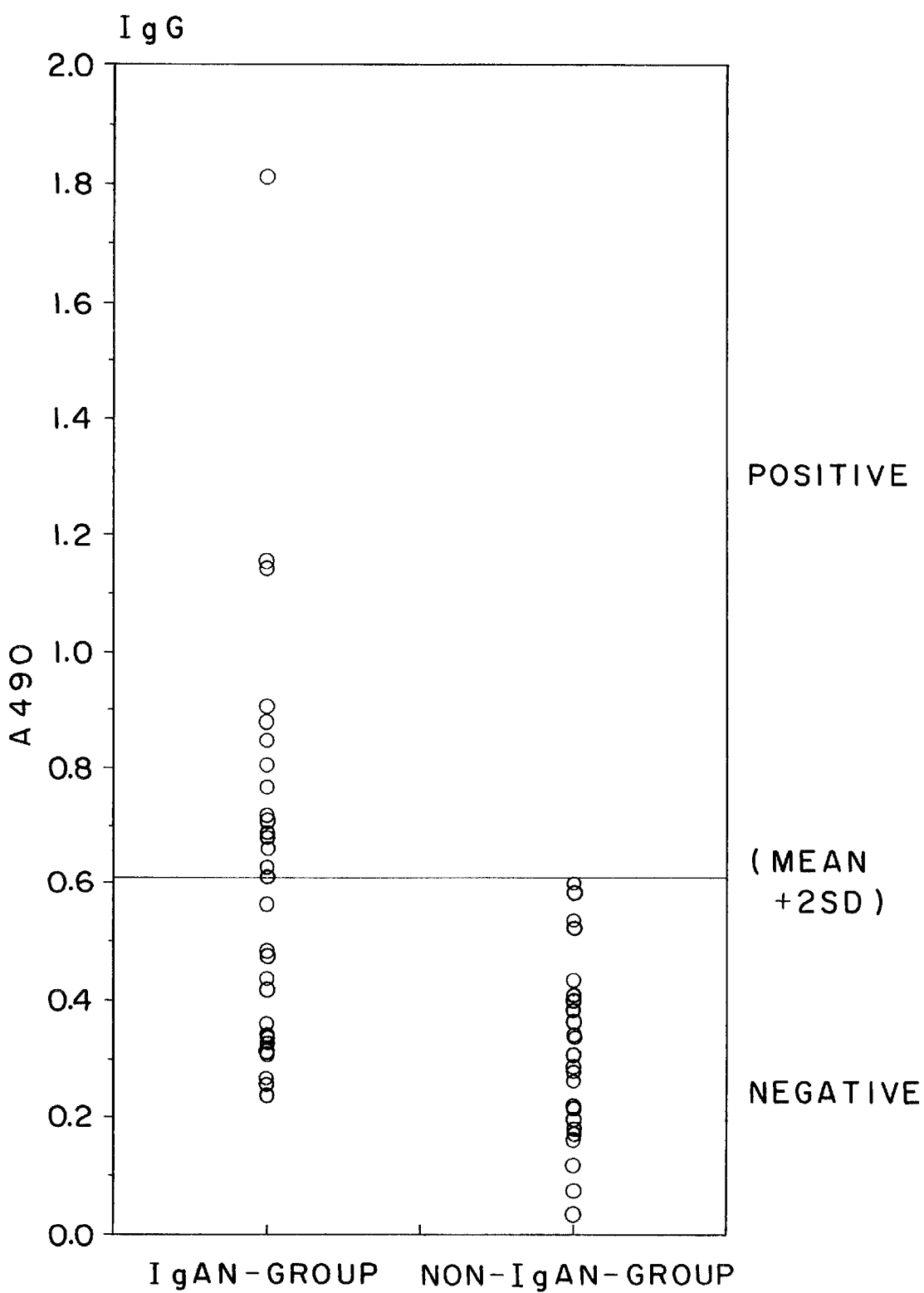
FIG. 2 is a graph plotting absorbancies of wave length at 490 nm in specimens of 32 patients with a group of IgA nephropathy and a group of non-IgA nephropathy in case of adding anti-human IgG.

FIG. 2 is a graph plotting absorbancies of wave length at 490 nm in specimens of 32 patients with a group of IgA nephropathy (in FIG. 2, IgAN group) and a group of non-IgA nephropathy (in FIG. 2, non-IgAN group) in case of adding peroxidase labeled anti-human IgG.

In this case, absorbancy showing above the average values (0.316) of 32 cases of a group of patients with non-IgA nephropathy+2×standard deviation=0.606 is set as positive.

As a result of the experiments, in the group of patients with non-IgA nephropathy, all of 32 cases were negative, on the contrary, in the group of patients with IgA nephropathy, 16 out of 32 cases were positive, and a statistically significant difference between the two groups was noted in the positive rate.

(4) Result of IgM Class Antibody Titer

Figure 3:
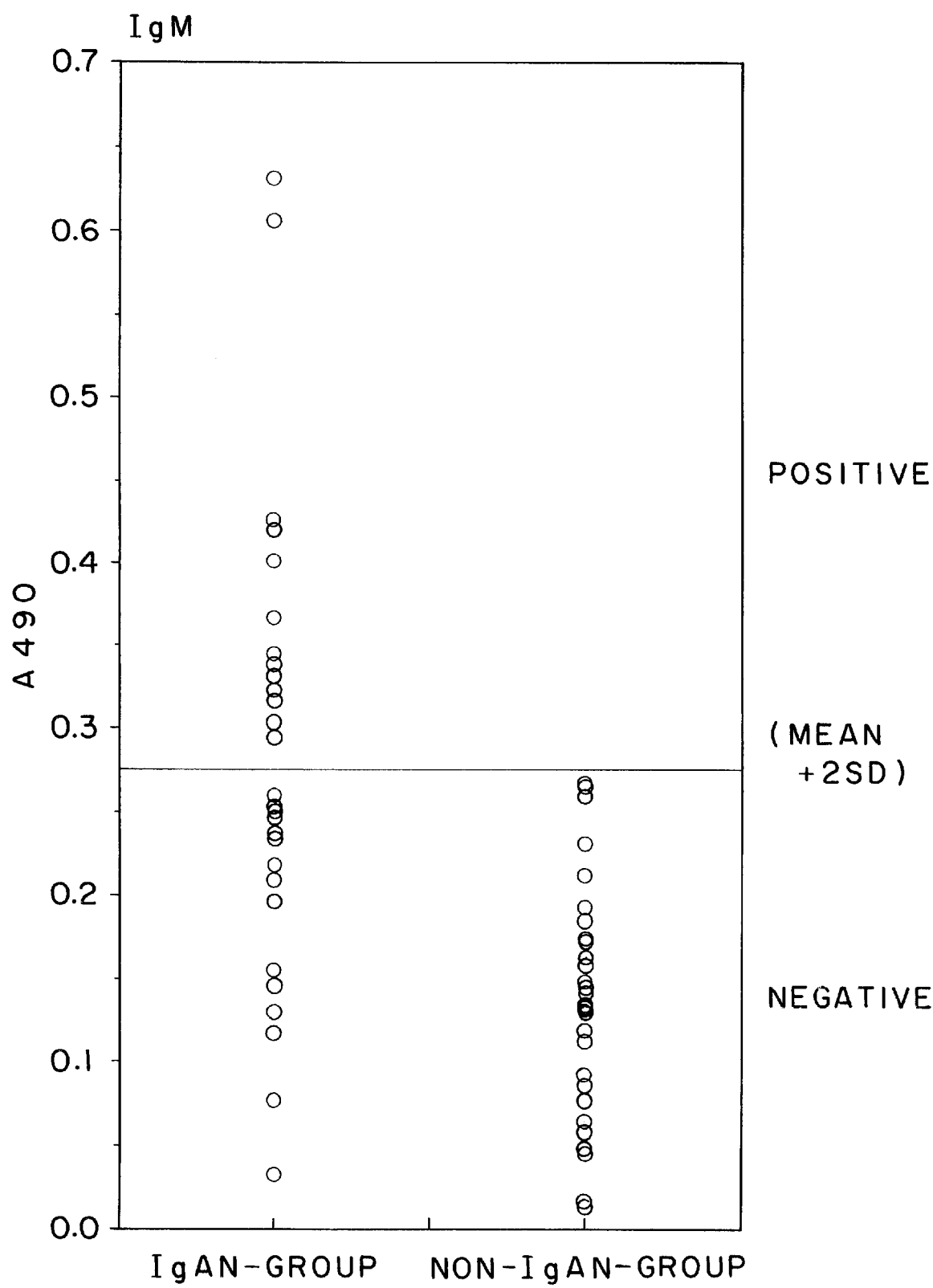
FIG. 3 is a graph plotting absorbancies of wave length at 490 nm in specimens of 32 patients with a group of IgA nephropathy and a group of non-IgA nephropathy in case of adding anti-human IgM.

FIG. 3 is a graph plotting absorbancies of wave length at 490 nm in specimens of 32 patients with a group of IgA nephropathy (in FIG. 3, IgAN group) and a group of non-IgA nephropathy (in FIG. 3, non-IgAN group) in case of adding peroxidase labeled anti-human IgM.

In this case, absorbancy showing above the average values (0.134) of 32 cases of a group of patients with non-IgA nephropathy+2×standard deviation=0.272 is set as positive.

As a result of the experiments, in the group of patients with non-IgA nephropahty, all of 32 cases were negative, on the contrary, in the group of patients with IgA nephropathy, 13 out of 32 cases were positive, and a statistically significant difference between the two groups was noted in the positive rate.

EXAMPLE 2

(1) Preparation of Antigen

Antigen was prepared according to the method described in the above example 1 (1).

(2) Assay of Inhibitory Activities of Various Synthetic Peptides

The above antigen solution was dissolved to 10 μl/ml in 0.015 M carbonate buffer (pH 9.6) and each 100 μl was added in each well of the 96 well microtiter plate (A Flow General Co., Linbro/Titertek EIA Microtitration plate, Cat. No. 76-381-04), then incubated at 4° C. overnight (standing culture).

PBS (0.01 M phosphate buffer, pH 7.5 containing 0.15 M NaCl) solution (200 μl) containing 1% bovine serum albumin (fraction V, purchased from SIGMA Inc.) was added in each well, and incubated at 4° C. overnight. Each well was washed with 200 μl of PBS. The antigen was immobilized.

Serum of a patient with IgA nephropathy which showed positive in example 1 was diluted to 1/50 with PBS. Synthetic peptide [the core peptide constructing a part of the hinge region in IgA1 as follows:

```
Pro Val Pro Ser Thr (SEQ ID NO: 2)(hereinafter designated as P V P S T)

Pro Ser Thr Pro Pro (SEQ ID NO: 3)(hereinafter designated as P S T P P)

Thr Pro Pro Thr Pro (SEQ ID NO: 4)(hereinafier designated as T P P T P)

Pro Thr Pro Ser Pro (SEQ ID NO: 5)(hereinafter designated as P T P S P)

Pro Ser Pro Ser Thr (SEQ ID NO: 6)(hereinafier designated as P S P S T)

Pro Ser Pro Ser Cys (SEQ ID NO: 7)(hereinafter designated as P S P S C)
``` and the core peptide constructing a part of the bovine serum albumin as follows:

```
Ser Pro Asp Leu Pro (SEQ ID NO: 8)(hereinafter designated as S P D L P);

Leu Lys Pro Asp Pro (SEQ ID NO: 9)(hereinafter designated as L K P D P);

Leu Pro Pro Leu Thr (SEQ ID NO: 10)(hereinafter designated as L P P L T);

Thr Pro Val Glu Ser (SEQ ID NO: 11)(hereinafier designated as T P V E S);

Thr Pro Asp Glu Thr (SEQ ID NO: 12)(hereinafter designated as T P D E T)]
``` was dissolved to 1 μg/ml with PBS. The above diluted serum of patient with IgA nephropathy and the solution of synthetic peptide were mixed in equal volume (1:1). Also the above diluted serum of patient with IgA nephropathy and PBS without containing synthetic peptide (hereinafter designated as blank solution) were mixed in equal volume (1:1). These mixtures were incubated at room temperature for 3 hours.

After termination of the incubation, each solution (100 μl) was added in each well, which was provided with the antigen immobilized therein, of the 96 well microtiter plate and incubated at room temperature for 3 hours.

Each well was washed three times with 200 μl of PBS containing 0.1% bovine serum albumin, 0.05% Tween-20 (hereinafter designated as PS/BSA/Tween).

A solution (100 μl) of peroxidase labeled anti-human IgG (purchased from Organon Tecknika Inc.), which was diluted to 1/200 with PBS, was added in each well.

After incubation at room temperature for 1 hour, each well was washed three times with PS/BSA/Tween (200 μl).

Coloring agent (100 μl)(orthophenylenediamine 20 mg, sodium dihydrogen phosphate·12$H_2$O 1.795 g, citric acid 0.525 g, and hydrogen peroxide 15 μl were dissolved in water 50 ml) was added in each well, and incubated at room temperature for 1 hour.

After the incubation was terminated, absorbency at 490 nm was measured using microplate reader (Bio-Red Inc., Microplate reader Model 450).

Figure 4:
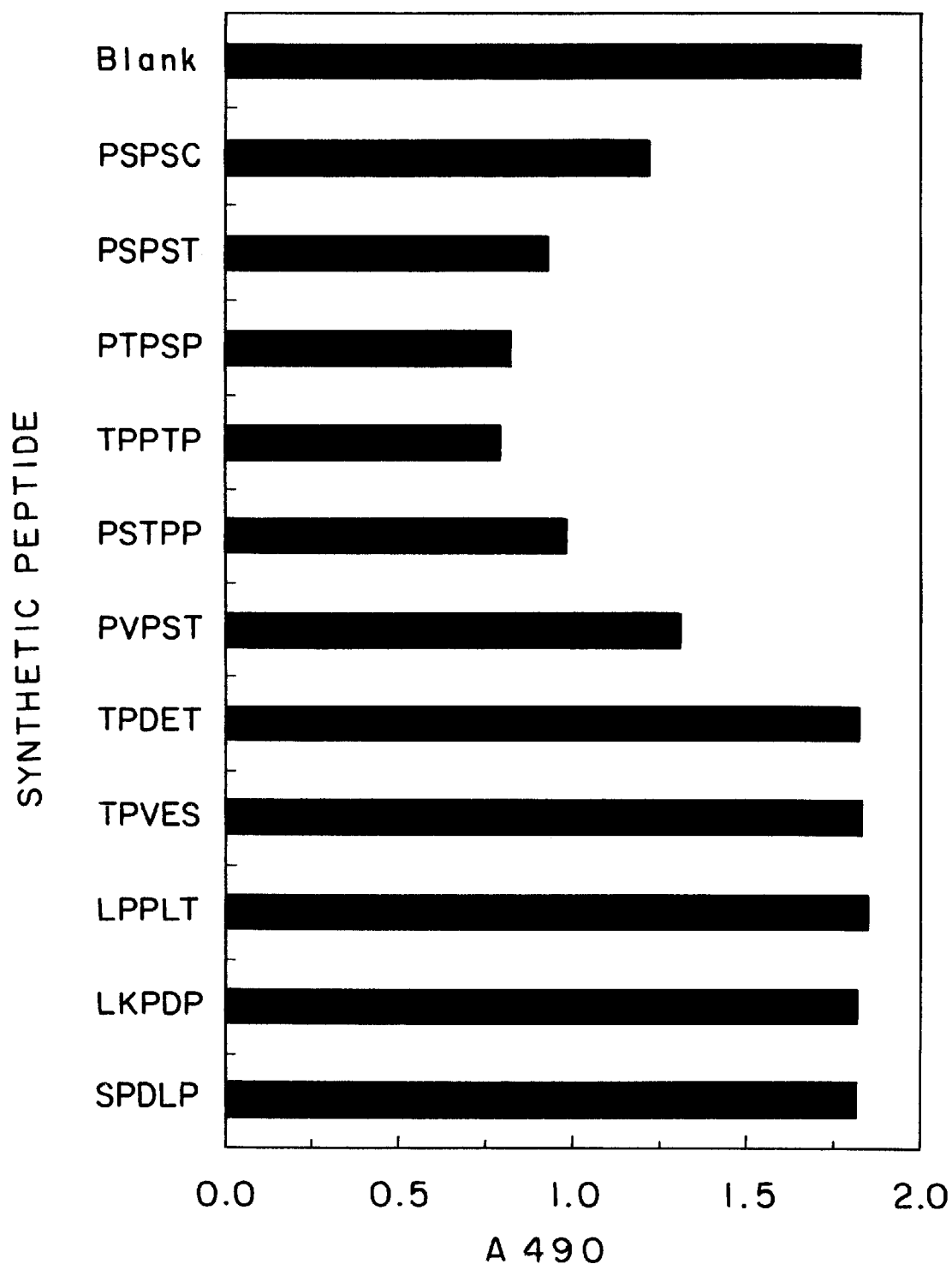
FIG. 4 is a graph plotting absorbancies at 490 nm showing the reactivity of the serum of patient with IgA nephropathy, previously reacted with various synthetic peptide or blank solution, and the core peptide of the hinge region in IgA1.

(3) Results of Measurement of Inhibitory Activities of Various Synthetic Peptides FIG. 4 is a graph plotting absorbancies at 490 nm showing the reactivity of the serum of patient with IgA nephropathy, previously reacted with various synthetic peptide or blank solution, and the core peptide of the hinge region in IgA1.

The results of the experiments indicated that no inhibitory action on the reaction was observed in case of adding the core peptide (in FIG. 4, SPDLP, LKPDP, LPPLT, TPVES and TPDET) constructing a partial structure of bovine serum albumin, and less than 10% of difference in the absorption between the added group and the blank solution (in FIG. 4, Blank) was noted.

On the other hand, when the core peptide (in FIG. 4, PVPST, PSTPP, TPPTP, PTPSP, PSPST and PSPSC) constructing a partial structure of the hinge region in IgA1 was added, the inhibitory action on the reaction was observed, and more than 10% of difference in the absorption between the added group and the blank solution (in FIG. 4, Blank) was noted.

It was demonstrated that as a result of the above experiments, the test method of the present invention could specifically measure the antibody recognizing the core peptide of the hinge region in IgA1, which was represented by the amino acid sequence of the formula Pro Val Pro Ser Thr Pro Pro Thr Pro Ser Pro Ser Thr Pro Pro Thr Pro Ser Pro Ser Cys (SEQ ID NO: 1)

in specimens, and when the peptide, which constructed a partial structure of the core peptide of the hinge region in IgA1 and consisting of at least 5 amino acids, was used, the test can be performed.

Sequence listings of the core peptide of the hinge region in IgA1 and the core peptide constructing a partial structure of bovine serum albumin are shown hereinbelow for reference.

EFFECT OF THE INVENTION

The test method of the present invention is advantageous as a rapid and simple test method for IgA nephropathy, since the test method has low risk of emotional distress for the patients, reduced risk of peripheral hemorrhage in the kidney and less financial burden to the patients, and operability with simple operation within short time.

What is claimed is:

1. A test method for detecting IgA nephropathy in a patient suspected of having IgA nephropathy comprising obtaining a sample comprising immunoglobulins from the patient, contacting the sample with a hinge-region core peptide of IgA1 comprising amino acid sequence SEQ ID NO:1 or a fragment thereof comprising at least five sequential amino acids, and determining presence or amount of antibody in the sample which specifically binds to the core peptide, wherein an increased amount of said antibody determined in the sample relative to an amount determined in control samples is indicative of IgA nephropathy in the patient.

2. The method of claim 1, wherein the core peptide is immobilized on a solid phase.

3. The method of claim 2, wherein the solid phase is selected from latex particles or a multi-well microtiter plate.

* * * * *

SEQUENCE LISTING

```
<160> NUMBER OF SEQ ID NOS: 13

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Formula
      amino acid sequence

<400> SEQUENCE: 1

Pro Val Pro Ser Thr Pro Pro Thr Pro Ser Pro Ser Thr Pro Pro Thr
 1               5                  10                  15

Pro Ser Pro Ser Cys
            20

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Formula
      amino acid sequence

<400> SEQUENCE: 2

Pro Val Pro Ser Thr
 1               5
```

```
<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Formula
      amino acid sequence

<400> SEQUENCE: 3

Pro Ser Thr Pro Pro
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Formula
      amino acid sequence

<400> SEQUENCE: 4

Thr Pro Pro Thr Pro
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Formula
      amino acid sequence

<400> SEQUENCE: 5

Pro Thr Pro Ser Pro
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Formula
      amino acid sequence

<400> SEQUENCE: 6

Pro Ser Pro Ser Thr
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Formula
      amino acid sequence

<400> SEQUENCE: 7

Pro Ser Pro Ser Cys
 1               5

<210> SEQ ID NO 8
<211> LENGTH: 5
<212> TYPE: PRT
<213> ORGANISM: Bovine sp.

<400> SEQUENCE: 8
```

```
Ser Pro Asp Leu Pro
  1               5

<210> SEQ ID NO 9
<211> LENGTH: 5
<212> TYPE: PRT
<213> ORGANISM: Bovine sp.

<400> SEQUENCE: 9

Leu Lys Pro Asp Pro
  1               5

<210> SEQ ID NO 10
<211> LENGTH: 5
<212> TYPE: PRT
<213> ORGANISM: Bovine sp.

<400> SEQUENCE: 10

Leu Pro Pro Leu Thr
  1               5

<210> SEQ ID NO 11
<211> LENGTH: 5
<212> TYPE: PRT
<213> ORGANISM: Bovine sp.

<400> SEQUENCE: 11

Thr Pro Val Glu Ser
  1               5

<210> SEQ ID NO 12
<211> LENGTH: 5
<212> TYPE: PRT
<213> ORGANISM: Bovine sp.

<400> SEQUENCE: 12

Thr Pro Asp Glu Thr
  1               5

<210> SEQ ID NO 13
<211> LENGTH: 19
<212> TYPE: PRT
<213> ORGANISM: Unknown Organism
<220> FEATURE:
<223> OTHER INFORMATION: Description of Unknown Organism: IgA1

<400> SEQUENCE: 13

Pro Ser Thr Pro Pro Thr Pro Ser Pro Ser Thr Pro Pro Thr Pro Ser
  1               5                  10                  15

Pro Ser Cys
```